US009629526B2

United States Patent
Ubayama et al.

(10) Patent No.: US 9,629,526 B2
(45) Date of Patent: Apr. 25, 2017

(54) ENDOSCOPE SYSTEM FOR CONTROLLING OUTPUT OF LASER FROM LASER PROBE

(71) Applicant: OLYMPUS CORPORATION, Tokyo (JP)

(72) Inventors: Nanako Ubayama, Hachioji (JP); Kotaro Ogasawara, Tokyo (JP); Kentaro Hase, Hachioji (JP); Hitoshi Komine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/929,491

(22) Filed: Nov. 2, 2015

(65) Prior Publication Data

US 2016/0051133 A1 Feb. 25, 2016

Related U.S. Application Data

(63) Continuation of application No. PCT/JP2014/070342, filed on Aug. 1, 2014.

(30) Foreign Application Priority Data

Aug. 7, 2013 (JP) .................................. 2013-164379

(51) Int. Cl.
*A61B 1/018* (2006.01)
*A61B 1/04* (2006.01)
(Continued)

(52) U.S. Cl.
CPC ............ *A61B 1/063* (2013.01); *A61B 1/0002* (2013.01); *A61B 1/00006* (2013.01);
(Continued)

(58) Field of Classification Search
None
See application file for complete search history.

(56) References Cited

U.S. PATENT DOCUMENTS 5,893,828 A * 4/1999 Uram ..................... A61B 18/22
600/108
7,869,016 B2 * 1/2011 Mitchell ................ A61B 18/22
219/121.62
(Continued)

FOREIGN PATENT DOCUMENTS

EP 2 550 909 A1 1/2013
JP H03-149022 A 6/1991
(Continued)

OTHER PUBLICATIONS

International Search Report dated Oct. 14, 2014 issued in PCT/JP2014/070342.

(Continued)

*Primary Examiner* — John P Leubecker
(74) *Attorney, Agent, or Firm* — Scully, Scott, Murphy & Presser, P.C.

(57) ABSTRACT

An endoscope system includes: an insertion portion; an illumination portion that emits a plurality of illuminating lights of different hues to each other; an image pickup portion that picks up an optical image formed by an objective optical system in a distal end portion of the insertion portion; a channel that opens in a distal end portion of the insertion portion; a laser probe that is inserted through the channel and has an irradiation portion in a distal end region; a hue range setting portion that sets a hue range of the laser probe in accordance with a hue of an illuminating light; an image analysis portion that detects a hue range portion in a color image obtained from the image pickup portion; and a control portion that permits laser output only in a case where the hue range portion is detected.

3 Claims, 5 Drawing Sheets

(51) Int. Cl.
*A61B 1/06* (2006.01)
*A61B 1/00* (2006.01)
*A61B 1/012* (2006.01)
*A61B 90/00* (2016.01)
*A61B 17/00* (2006.01)
*A61B 18/00* (2006.01)
*A61B 18/20* (2006.01)

(52) U.S. Cl.
CPC ...... *A61B 1/00009* (2013.01); *A61B 1/00096* (2013.01); *A61B 1/012* (2013.01); *A61B 1/018* (2013.01); *A61B 1/04* (2013.01); *A61B 1/0638* (2013.01); *A61B 90/37* (2016.02); *A61B 18/201* (2013.01); *A61B 2017/0034* (2013.01); *A61B 2017/00123* (2013.01); *A61B 2018/00708* (2013.01); *A61B 2018/00982* (2013.01)

(56) References Cited

U.S. PATENT DOCUMENTS

| | | | | |
|---|---|---|---|---|
| 2002/0188285 | A1* | 12/2002 | Brown | A61B 1/0051 606/15 |
| 2004/0034277 | A1* | 2/2004 | Farkas | A61B 1/063 600/108 |
| 2009/0088634 | A1* | 4/2009 | Zhao | B25J 9/1689 600/427 |
| 2009/0198104 | A1* | 8/2009 | Sugiyama | A61B 1/00039 600/146 |
| 2012/0182409 | A1* | 7/2012 | Moriyama | A61B 1/00006 348/65 |
| 2013/0002844 | A1 | 1/2013 | Shida | |
| 2013/0038708 | A1* | 2/2013 | Iwasaki | A61B 1/00006 348/65 |
| 2013/0072753 | A1* | 3/2013 | Zappia | A61B 1/0008 600/108 |
| 2015/0133728 | A1* | 5/2015 | Finkman | A61B 18/245 600/108 |

FOREIGN PATENT DOCUMENTS

| | | |
|---|---|---|
| JP | H04-325139 A | 11/1992 |
| JP | H08-280709 A | 10/1996 |
| JP | H10-276974 A | 10/1998 |
| JP | 2002-125926 A | 5/2002 |
| JP | 2006-271871 A | 10/2006 |
| JP | 2008-212349 A | 9/2008 |
| WO | WO 2011/118287 A1 | 9/2011 |

OTHER PUBLICATIONS

Japanese Office Action dated Apr. 28, 2015 issued in JP 2015-507289.

Extended Supplementary European Search Report dated Dec. 20, 2016 in European Patent Application No. 14 83 3957.5.

* cited by examiner

ENDOSCOPE SYSTEM FOR CONTROLLING OUTPUT OF LASER FROM LASER PROBE

CROSS REFERENCE TO RELATED APPLICATION

This application is a continuation application of PCT/JP2014/070342 filed on Aug. 1, 2014 and claims benefit of Japanese Application No. 2013-164379 filed in Japan on Aug. 7, 2013, the entire contents of which are incorporated herein by this reference.

BACKGROUND OF THE INVENTION

1. Field of the Invention

The present invention relates to an endoscope system including an endoscope and a laser probe that is inserted through an endoscope channel, and an operation method for the endoscope system.

2. Description of the Related Art

Medical treatment is sometimes performed by inserting a treatment instrument through a channel provided in an endoscope, and causing the distal end of the treatment instrument to protrude from the distal end of the endoscope.

Since the aforementioned kind of treatment instrument is generally used in a state in which the distal end thereof has been caused to protrude from the distal end of an endoscope, it is desirable to check the protruding state thereof. Therefore, various kinds of technology have been proposed for detecting that a treatment instrument is protruding from the distal end of an endoscope.

For example, Japanese Patent Application Laid-Open Publication No. 2002-125926 discloses technology in which the protrusion of a treatment instrument from the distal end of an endoscope is detected by a sensor such as a photo-interrupter. According to the technology described in the aforementioned publication, the detection result is used for controlling the magnification of an image.

Further, Japanese Patent Application Laid-Open Publication No. 2008-212349 discloses technology that includes a forceps roller that is arranged in a proximal end portion of a forceps channel, a forceps encoder for detecting a rotation angle of the forceps roller, and a forceps detecting apparatus that detects the protrusion or retraction of a forceps from or into a distal end portion of the forceps channel based on rotation angle data from the forceps encoder. According to the technology disclosed in the aforementioned publication, a detection result is used, for example, for an animated display of the protruding state of the forceps. In addition, in the aforementioned publication, technology is disclosed whereby, in a case where a detection result is that the forceps is not protruding, the operation transitions to a stop mode to prohibit the passage of a high-frequency current to the treatment instrument.

In addition, in Japanese Patent Application Laid-Open Publication No. 2006-271871 technology is described that determines that a treatment instrument is positioned in the vicinity of a target site in a case where a signal of a predetermined luminance value or more is detected in a predetermined region within an observation field of view. According to the technology described in the aforementioned publication, a determination result is used as a trigger for starting video recording.

In this connection, in some treatment instruments a treatment portion for treating a subject by imparting energy to the subject is provided at the distal end of the treatment instrument. Examples of such treatment instruments include a laser probe that is described in the aforementioned Japanese Patent Application Laid-Open Publication No. 2002-125926, or a high-frequency treatment instrument that is described in the aforementioned Japanese Patent Application Laid-Open Publication No. 2002-125926 or Japanese Patent Application Laid-Open Publication No. 2008-212349. Surgery that pulverizes a stone by means of a laser in transurethral ureterolithotripsy may be mentioned as an example of treatment in which the laser probe of the former is utilized.

Further, endoscopes sometimes perform observation in a plurality of observation modes. Some examples of such observation modes that may be mentioned include a white light observation mode, an NBI observation mode and a fluorescence observation mode. With regard to the illuminating light emitted towards a subject, illuminating lights of different hues are emitted in accordance with which observation mode is used to perform the observation. For example, red (R) illuminating light, green (G) illuminating light and blue (B) illuminating light are emitted in the white light observation mode, and narrow-band blue light and narrow-band green light that are easily absorbed by hemoglobin are emitted in the NBI observation mode.

SUMMARY OF THE INVENTION

An endoscope system according to a certain aspect of the present invention includes: an insertion portion that is inserted into a subject; an illumination portion that emits a first illuminating light or a second illuminating light of a different hue to the first illuminating light towards the subject; an objective optical system that is provided in a distal end portion of the insertion portion; an image pickup portion that picks up an optical image of the subject that is formed by the objective optical system; a channel that is provided inside the insertion portion so as to have a channel opening in the distal end portion of the insertion portion; a laser probe that is inserted through the channel and that has, in a distal end region, an irradiation portion that outputs a laser towards the subject; a hue range setting portion that sets a hue range in which a hue can be estimated as being a hue of the laser probe in accordance with whether an illuminating light emitted from the illumination portion is the first illuminating light or the second illuminating light; an image analysis portion that detects a portion of the hue range in a color image that is obtained as an image pickup result of the image pickup portion; and a control portion that, only in a case where a portion of the hue range is detected by the image analysis portion, determines that the irradiation portion of the laser probe protrudes from the channel opening and permits the laser probe to output the laser.

Further, an operation method for an endoscope system according to a certain aspect of the present invention is an operation method for an endoscope system, the endoscope system including: an insertion portion that is inserted into a subject; an illumination portion that emits a first illuminating light or a second illuminating light of a different hue to the first illuminating light towards the subject; an objective optical system that is provided in a distal end portion of the insertion portion; a channel that is provided inside the insertion portion so as to have a channel opening in the distal end portion of the insertion portion; and a laser probe that is inserted through the channel and that has, in a distal end region, an irradiation portion that outputs a laser towards the subject, the operation method comprising: an image pickup step in which an image pickup portion picks up an optical image of the subject that is formed by the objective optical system; a hue range setting step in which a hue range setting portion sets a hue range in which a hue can be estimated as being a hue of the laser probe in accordance with whether an illuminating light emitted from the illumination portion is the first illuminating light or the second illuminating light; an image analysis step in which an image analysis portion detects a portion of the hue range in a color image that is obtained as an image pickup result of the image pickup portion; and a control step in which, only in a case where a portion of the hue range is detected by the image analysis step, a control portion determines that the irradiation portion of the laser probe protrudes from the channel opening and permits the laser probe to output the laser.

DETAILED DESCRIPTION OF THE PREFERRED EMBODIMENTS

An embodiment of the present invention will be described hereunder with reference to the drawings.

Embodiment 1

Figure 1:
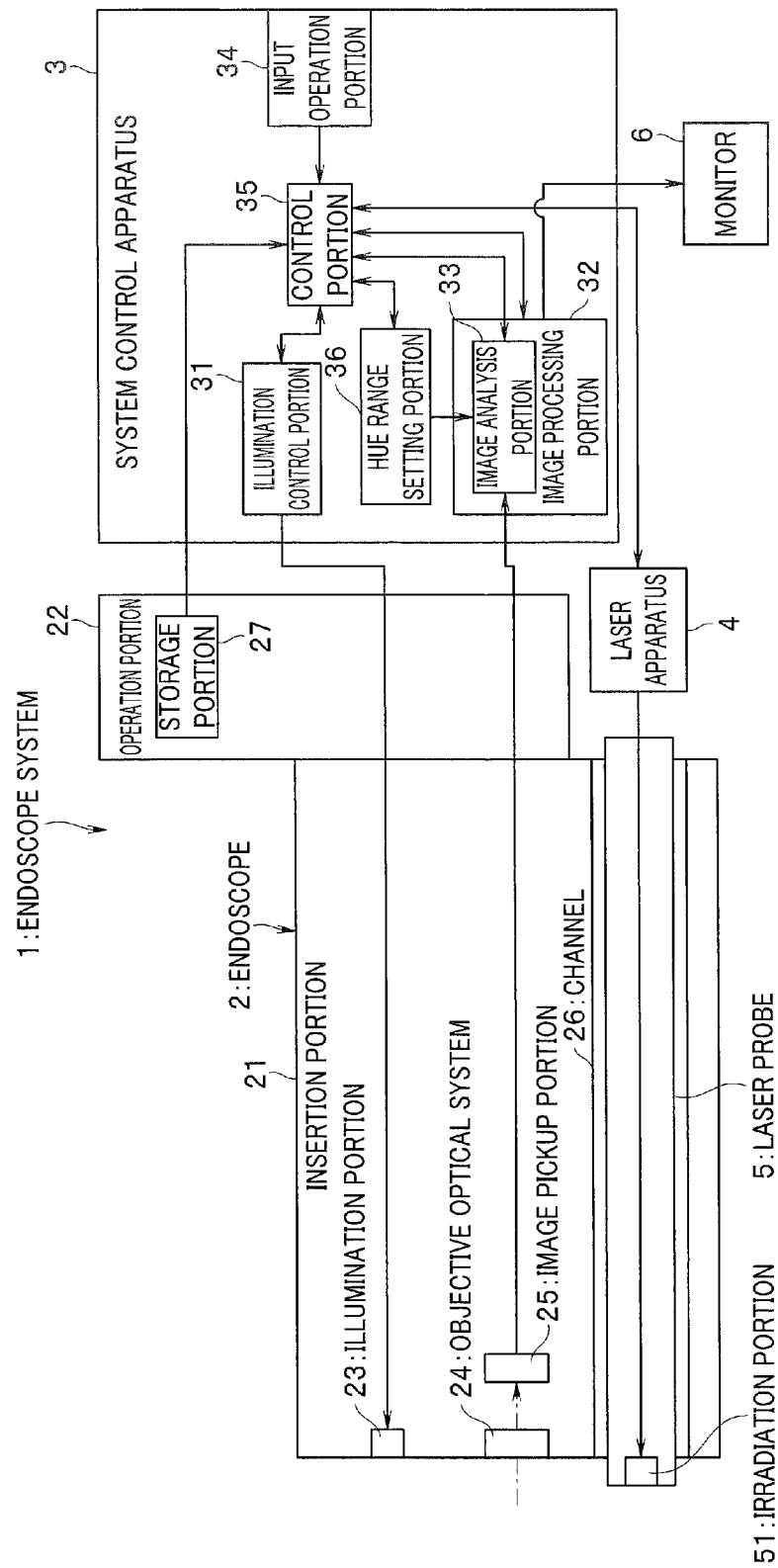
FIG. 1 is a block diagram illustrating the configuration of an endoscope system according to Embodiment 1 of the present invention.

FIG. 1 to FIG. 7 illustrate Embodiment 1 of the present invention. FIG. 1 is a block diagram showing the configuration of an endoscope system.

An endoscope system 1 includes an endoscope 2, a system control apparatus 3, a laser apparatus 4, a laser probe 5 and a monitor 6.

The endoscope 2 includes an elongated insertion portion 21 that extends from an operation portion 22 on a hand side towards a distal end side, and that is provided for insertion into a subject.

An illumination portion 23, an objective optical system 24 and an image pickup portion 25 are arranged in a distal end portion of the insertion portion 21.

The illumination portion 23 emits a plurality of kinds of illuminating light which are of different hues to each other towards a subject (among these plurality of kinds of illuminating light, a first illuminating light is taken as an arbitrary one kind of illuminating light, and a second illuminating light is taken as another arbitrary one kind of illuminating light).

The objective optical system 24 forms an optical image of an illuminated subject.

The image pickup portion 25 picks up the optical image of the subject that is formed by the objective optical system 24 and, for example, includes an image pickup device in which a plurality of pixels are arrayed. When the image pickup portion 25 performs an operation to pick up an image, for example, a color image is obtained as the image pickup result. That is, in a case where the image pickup portion 25 includes a single color image pickup device (in the case of a simultaneous method), a color image is obtained by a single image pick-up operation, and in a case where the image pickup portion 25 operates according to a frame sequential method, a single color image is obtained based on image pickup results obtained over a plurality of image pick-up operations (for example, 3 operations).

Further, in the insertion portion 21, a channel 26 for inserting a treatment instrument from the hand side to the distal end side is provided so as to have a channel opening (hereunder, referred to as "distal end opening") in the distal end portion of the insertion portion 21.

A storage portion 27 that stores endoscope type information such as an endoscope ID is provided in the operation portion 22 of the endoscope 2.

The above described endoscope 2 is configured so as to be connected to and controlled by the system control apparatus 3.

The system control apparatus 3 includes an illumination control portion 31, an image processing portion 32 including an image analysis portion 33, an input operation portion 34, a control portion 35 and a hue range setting portion 36.

The illumination control portion 31 controls the emission/non-emission of an illuminating light from the illumination portion 23, and the amount of illuminating light at a time of emission and the like, and also performs light emission control in accordance with observation modes that are described later.

The hue range setting portion 36 sets a hue range in which a hue can be estimated as being a hue of the laser probe 5 in accordance with whether an illuminating light emitted from the illumination portion 23 is the first illuminating light or the second illuminating light.

The image processing portion 32 subjects an image outputted from the image pickup portion 25 to image processing such as color balance adjustment, gamma conversion, color conversion and conversion to a signal format for displaying on the monitor 6, and outputs the resulting image signal to the monitor 6.

The image analysis portion 33 included in the image processing portion 32 performs image analysis on images, and detects an image portion showing the laser probe 5 in a color image that is obtained as an image pickup result of the image pickup portion 25. More specifically, the image analysis portion 33 analyses a color image and detects a portion in a hue range that has been set by the hue range setting portion 36 in the image.

The input operation portion 34 is a component for performing an operation input with respect to the system control apparatus 3, and is configured so as to enable the performance of operations to switch the power on and off and to set an observation mode and the like. Although the present embodiment is described on the basis that the observation modes that can be set in the endoscope system 1 are a white light observation mode and an NBI observation mode, a configuration may also be adopted in which other observation modes can be set in the endoscope system 1.

The control portion 35 controls the illumination control portion 31 so as to cause the illumination portion 23 to emit an illuminating light of a kind that is in accordance with the observation mode that is set. Further, the control portion 35 determines that the laser probe 5 is protruding from the distal end opening of the channel 26 and permits the laser probe 5 to output a laser only in a case where a portion of a hue range in which a hue can be estimated as being the hue of the laser probe 5 is detected by the image analysis portion 33. Accordingly, if the control portion 35 determines that the laser probe 5 is not protruding from the distal end opening of the channel 26, the control portion 35 prohibits laser output by the laser probe 5. In addition, based on endoscope type information that is acquired from the storage portion 27, the control portion 35 sets a detection region SA (see FIG. 2) in an image of the laser probe 5 that is protruded from the distal end opening of the channel 26, and controls so as to cause the image analysis portion 33 to perform detection of the hue range based only on the detection region SA that is set.

The laser probe 5 is configured to be inserted through the channel 26 of the endoscope 2, and includes, in a distal end region thereof, an irradiation portion 51 for outputting a laser towards a subject. Here, the term "distal end region" of the laser probe 5 refers to a region that, to a certain extent, is in the vicinity of the distal end of the laser probe 5, and for example, includes a portion that irradiates a laser to the side.

The laser apparatus 4 controls the laser output from the irradiation portion 51.

The monitor 6 is a color display apparatus that is connected to the system control apparatus 3 and that displays an endoscopic image processed by the image processing portion 32 and various kinds of information relating to the endoscope system 1.

Figure 5:
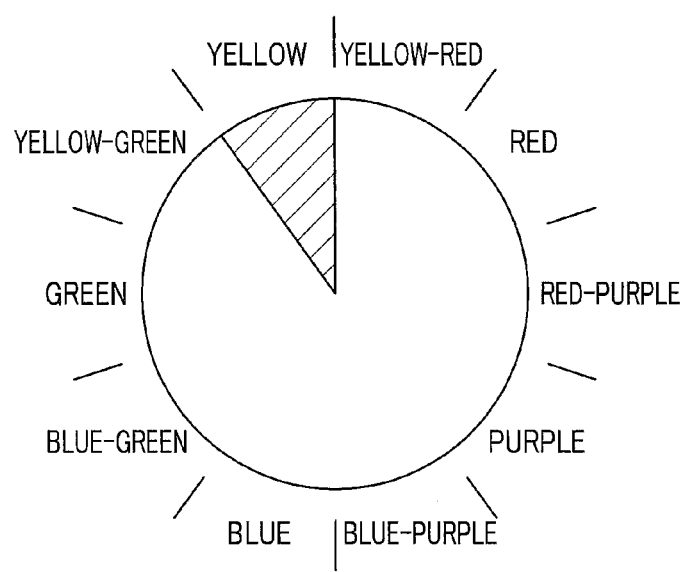
FIG. 5 is a view illustrating an example of a hue range of a laser probe that is set in the white light observation mode in the aforementioned Embodiment 1.
Figure 6:
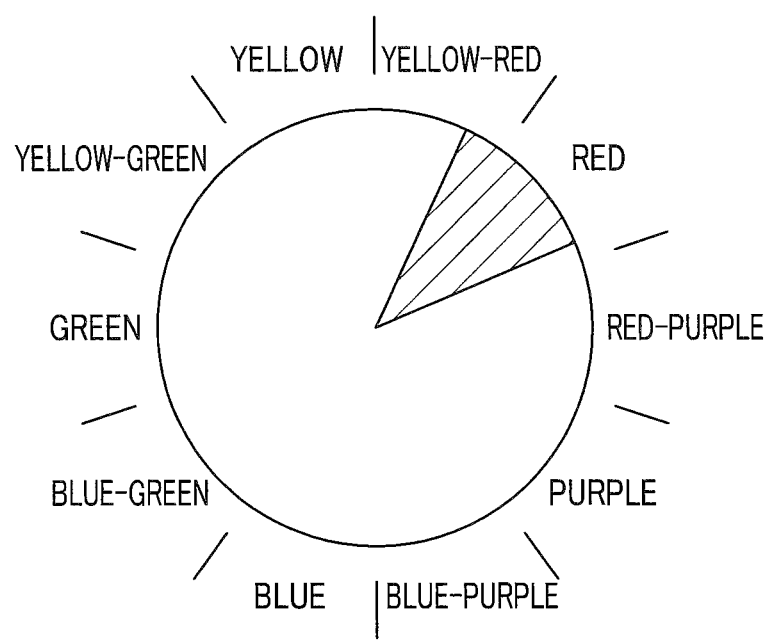
FIG. 6 is a view illustrating an example of a hue range of a laser probe that is set in the NBI observation mode in the aforementioned Embodiment 1.
Figure 7:
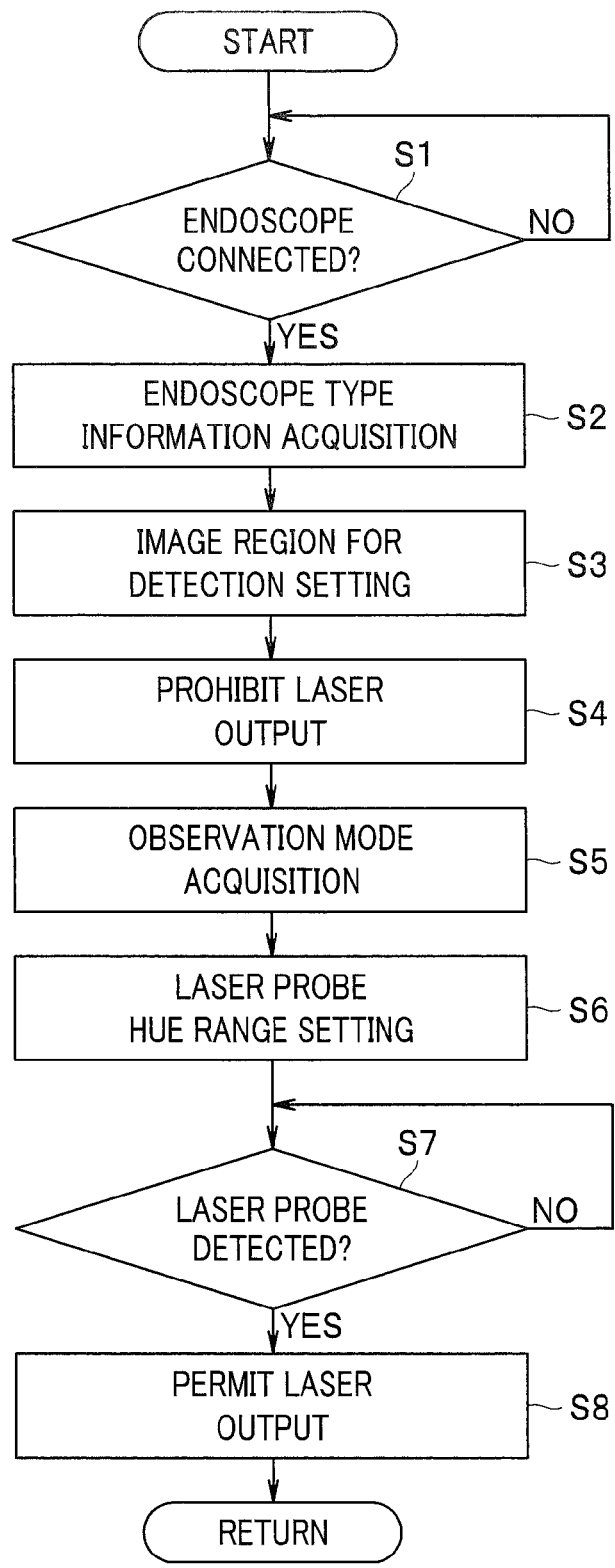
FIG. 7 is a flowchart illustrating operations of the endoscope system in the aforementioned Embodiment 1.

The operations of the endoscope system 1 (and by extension, an operation method for the endoscope system) will now be described in accordance with FIG. 7 while referring as appropriate to FIG. 2 to FIG. 6. FIG. 7 is a flowchart illustrating the operations of the endoscope system.

The processing shown in FIG. 7 is, for example, called from a main control processing routine for controlling the system control apparatus 3 (or the overall endoscope system 1) and executed.

Upon the start of the processing shown in FIG. 7, first, the system control apparatus 3 detects whether or not the endoscope 2 is connected (step S1).

If connection of the endoscope 2 is not detected, the system control apparatus 3 stands by until the endoscope 2 is connected. Upon connection of the endoscope 2 being detected in this manner, the control portion 35 acquires endoscope type information from the storage portion 27 of the endoscope 2 (step S2).

Figure 2:
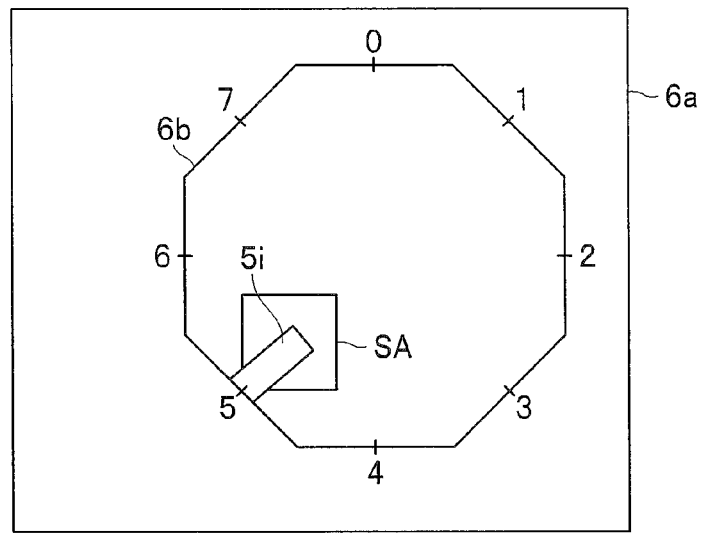
FIG. 2 is a view for describing the manner in which, in the aforementioned Embodiment 1, a detection region for detecting a laser probe is set according to the kind of endoscope.

FIG. 2 is a view for describing the manner in which a detection region SA for detecting the laser probe 5 is set according to the kind of the endoscope 2. In FIG. 2 (and FIG. 3 and FIG. 4 that are described later), reference character 6a denotes a screen of the monitor 6, and reference character 6b denotes an image display region for displaying an endoscopic image on the monitor screen 6a.

The positional relation between the objective optical system 24 and image pickup portion 25 and the distal end opening of the channel 26 in the endoscope 2 is determined according to the kind of the endoscope 2. Therefore a direction in the image display region 6b (directions indicated by numerals 0 to 7 in FIG. 2) from which the laser probe 5 will be displayed in the image is previously decided (in the example illustrated in FIG. 2, the direction from which the laser probe 5 is displayed in the image is indicated by the numeral 5).

Therefore, the control portion 35 sets the detection region SA in the image for the laser probe 5 that will be protruded from the distal end opening of the channel 26 based on the endoscope type information that is acquired in step S2 (step S3). At this time, the control portion 35 controls the image analysis portion 33 so as to cause the image analysis portion 33 to perform detection of the hue range with respect only to the detection region SA that is set.

Note that, although in this case the detection region SA is set so as to reduce the processing load and perform detection of the laser probe 5 at a high speed, naturally it is also possible to omit the processing in step S3 and adopt the entire image as the detection region.

Next, the control portion 35 controls the laser apparatus 4 so as to prohibit output of a laser from the irradiation portion 51 (step S4).

The control portion 35 next acquires the observation mode that is currently set in the system control apparatus 3 (step S5), causes the illumination portion 23, via the illumination control portion 31, to emit illuminating light of a hue that is in accordance with the observation mode (illumination step), and causes the image pickup portion 25 to pick up an optical image of the subject (image pickup step).

Based on the control of the control portion 35, the hue range setting portion 36 sets a hue range in which a hue can be estimated as being the hue of the laser probe 5 that is obtained as an endoscopic image, based on the kind of illuminating light that is in accordance with the observation mode that is set and at least the surface color of the distal end portion of the laser probe 5 (step S6) (hue range setting step).

Figure 3:
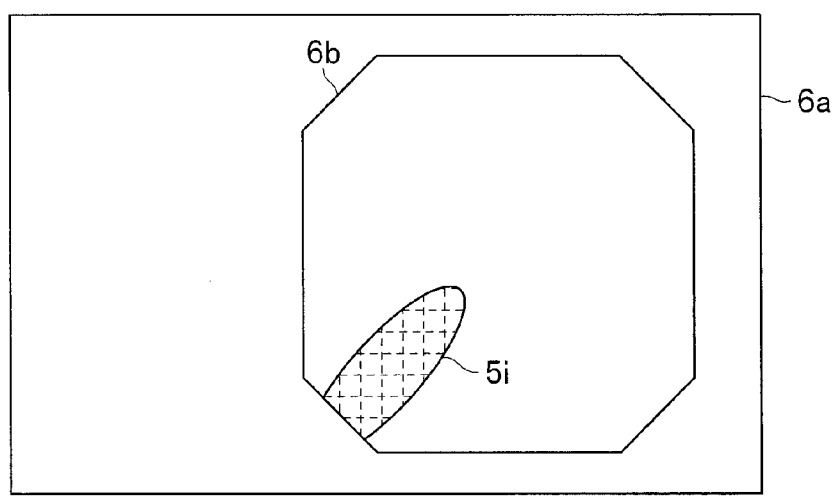
FIG. 3 is a view illustrating an example of an image of a laser probe in a white light observation mode in the aforementioned Embodiment 1.
Figure 4:
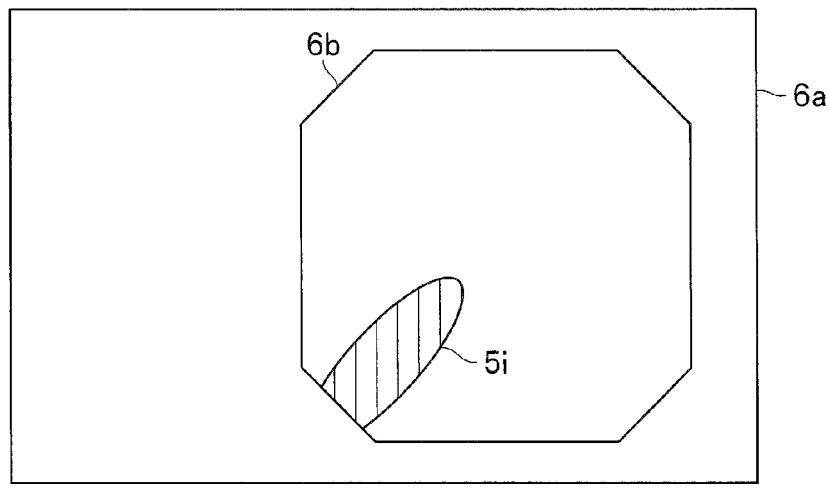
FIG. 4 is a view illustrating an example of an image of a laser probe in an NBI observation mode in the aforementioned Embodiment 1.

FIG. 3 is a view illustrating an example of an image of the laser probe 5 in the white light observation mode. FIG. 4 is a view illustrating an example of an image of the laser probe 5 in the NBI observation mode. FIG. 5 is a view illustrating an example of a hue range of the laser probe 5 that is set in the white light observation mode. FIG. 6 is a view illustrating an example of a hue range of the laser probe 5 that is set in the NBI observation mode.

In the white light observation mode, red (R) illuminating light, green (G) illuminating light and blue (B) illuminating light are emitted, and the light amount balance for the respective color is balanced so as to form white light when light of the respective colors is emitted simultaneously. In the white light observation mode, for example, a yellow image is obtained as the image portion 5i of the laser probe 5 shown in FIG. 3. Therefore, the hue range setting portion 36 sets a yellow hue range as indicated by a hatching section in FIG. 5 as a hue range in which a hue can be estimated as being the hue of the laser probe 5.

In contrast, in the NBI observation mode, narrow-band blue light and narrow-band green light that are easily absorbed by hemoglobin are emitted. In the NBI observation mode, for example, a red image is obtained as the image portion 5i of the laser probe 5 shown in FIG. 4. Therefore, the hue range setting portion 36 sets a red hue range as indicated by a hatching section in FIG. 6 as a hue range in which a hue can be estimated as being the hue of the laser probe 5.

Next, the control portion 35 determines whether or not the laser probe 5 has protruded from the distal end opening of the channel 26 by determining whether or not a part of the hue range that was set in step S6 has been detected in the detection region SA that was set in step S3 (step S7) (image analysis step). More specifically, the control portion 35 determines that the laser probe 5 is detected only in a case where, among all the pixels constituting the detection region SA, a predetermined number of pixels or more are included in the hue range in which a hue can be estimated as being the hue of the laser probe 5. The reason that a predetermined number of pixels or more is adopted in this case is to ensure reliable detection and also because it is considered that a number of pixels that is greater than or equal to a predetermined number will be detected in a case where the laser probe 5 protrudes by a necessary amount from the distal end opening of the channel 26.

Further, to perform an even more reliable detection, a configuration may also be adopted in which a contour is detected in combination with the hue. More specifically, the image analysis portion 33 detects contours of portions at which pixels in a hue range in which a hue can be estimated as being the hue of the laser probe 5 are continuous from within the detection region SA in the image, and determines whether or not a contour exists that is similar to the contour of the distal end portion of the laser probe 5 among the detected contours. The control portion 35 may then determine that the laser probe 5 has protruded from the distal end opening of the channel 26 only if a contour exists that is similar to the contour of the distal end portion of the laser probe 5. By further adopting such a configuration, in a case where a hue portion that is similar to the hue of the laser probe 5 may be present in the subject also, it is possible to reduce the occurrence of erroneous detection of the aforementioned subject portion as the laser probe 5, and thereby further increase the detection accuracy with respect to the laser probe 5.

In a case where the laser probe 5 is detected in this manner in step S7, the control portion 35 permits the laser apparatus 4 to output a laser from the laser probe 5 (step S8) (control step), and then returns to the main control processing routine from this processing.

According to Embodiment 1 that is configured as described above, since whether or not the laser probe 5 is protruding from the distal end opening of the channel 26 is detected, and laser output is permitted only in a case where protrusion of the laser probe 5 has been detected, laser output is not performed inside the channel 26 and thus damage to the endoscope 2 can be prevented and the safety thereof can be enhanced.

Because detection of a protruding state of the laser probe 5 from the distal end opening of the channel 26 is performed by image analysis, a dedicated sensor or the like is not required, and hence the weight and cost of the endoscope can be reduced. Further, a situation can be avoided in which a sensor malfunctions and detection of a protruding state of the laser probe 5 is not possible or the like. Furthermore, it is possible not only to detect whether or not the laser probe 5 is protruding, but also to easily confirm the amount by which the laser probe 5 protrudes from the distal end opening of the channel 26.

In addition, since detection is performed based on the hue, it is possible to reliably detect the laser probe 5 whose hue is clearly different from a subject such as a living organism (or the laser probe 5 that can be easily formed so that the hue thereof is clearly different from the subject).

At such time, since a hue range in which a hue can be estimated as being the hue of the laser probe 5 is appropriately set in accordance with the kind of illuminating light, even when illuminating light of a different hue is emitted, it is possible to detect the laser probe 5 with high accuracy.

In addition, since a configuration is adopted so as to detect the laser probe 5 from the detection region SA that is set in accordance with the endoscope type information, in comparison to a case of detecting the laser probe 5 from the entire region of the image, the processing load is reduced and detection can be performed in a shorter time.

Therefore, it is possible to accurately detect the laser probe 5 in an image regardless of the illuminating light, and to thus use the laser probe 5 more safely.

Note that although an endoscope system has been mainly described in the foregoing description, the present invention may be an operation method that causes an endoscope system to operate as described above, or a processing program for causing a computer to cause an endoscope system to operate as described above, or a non-transitory computer-readable recording medium that records the processing program or the like.

Note that the present invention is not limited to the precise embodiment described above, and can be embodied in the implementing stage by modifying the components without departing from the scope of the invention. Also, various aspects of the invention can be formed by appropriately combining a plurality of the components disclosed in the embodiment described above. For example, some components may be deleted from all of the disclosed components according to the embodiment. Furthermore, components from different embodiments may be appropriately combined. Thus, naturally, various modifications and applications are possible within a range that does not deviate from the spirit and scope of the present invention.

What is claimed is:

1. An endoscope system, comprising:
   an insertion portion configured to be inserted into a subject;
   an illuminating light source configured to emit a first illuminating light towards the subject and to emit a second illuminating light of a different hue to the first illuminating light towards the subject;
   an objective optical system provided in a distal end portion of the insertion portion, wherein the objective optical system is configured to form an optical image of the subject;
   an image sensor configured to pick up the optical image of the subject formed by the objective optical system, to obtain a color image;
   a channel provided inside the insertion portion so as to have a channel opening in the distal end portion of the insertion portion;
   a laser probe configured to be inserted through the channel, wherein the laser probe is configured to be controlled to output a laser, and wherein the laser probe comprises, in a distal end region of the laser probe, an irradiation end face through which the laser is outputted; and
   a processor comprising hardware, wherein the processor is configured to:
      set a hue range in which a hue can be estimated as being a hue of the laser probe, wherein the hue range is set in accordance with whether an illuminating light emitted from the illuminating light source is the first illuminating light or the second illuminating light;
      detect a portion of the hue range in the color image that is obtained by the image sensor; and
      only in a case where the portion of the hue range is detected, determine that the irradiation end face of the laser probe protrudes from the channel opening and permits the laser probe to output the laser.

2. The endoscope system according to claim 1, further comprising a storage circuit configured to store endoscope type information, and wherein based on the endoscope type information, the processor is configured to set a detection region in the color image for the laser probe that is protruded from the channel opening, and perform detection of the portion of the hue range with respect to only the detection region that is set.

3. The endoscope system according to claim 1, wherein the processor is configured to:

detect contours of portions at which pixels of the hue range are continuous from within the color image, and determine whether or not a contour that is similar to a contour of the distal end region of the laser probe exists among the detected contours; and only in a case where the similar contour exists, further determine that the irradiation end face of the laser probe protrudes from the channel opening and permit the laser probe to output the laser.

* * * * *